Dec. 5, 1967 H. B. LEWIS ETAL Plant Pat. 2,782
AZALEA PLANT
Filed Sept. 28, 1966
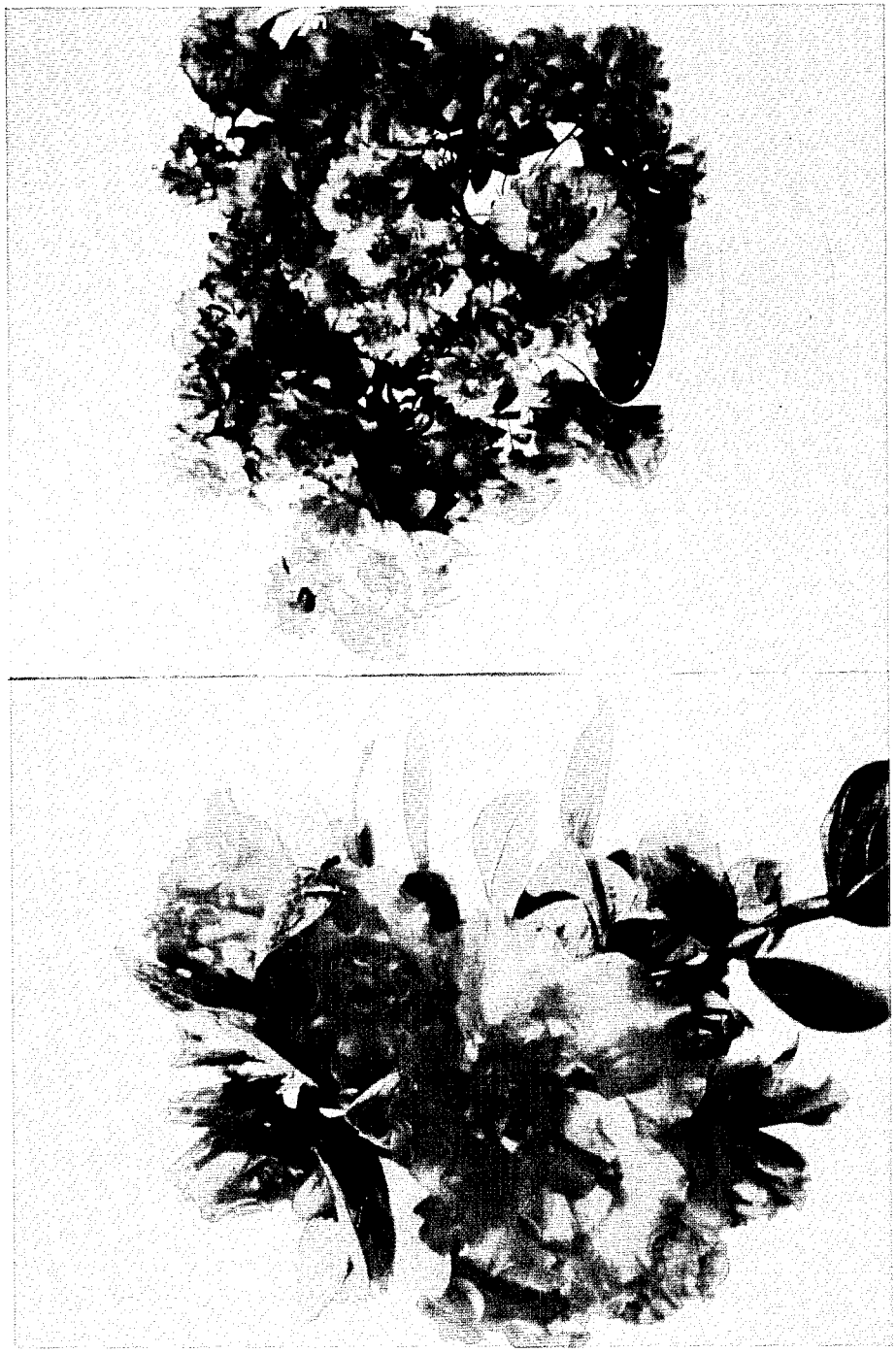
Inventors.
H. B. Lewis
H. H. Lewis
By: Robb & Robb
Attorneys.

United States Patent Office

Plant Pat. 2,782
Patented Dec. 5, 1967

2,782
AZALEA PLANT

Hubert B. Lewis and Helen H. Lewis, both of 16562 E. Leffingwell Road, Whittier, Calif. 90603

Filed Sept. 28, 1966, Ser. No. 582,768
1 Claim. (Cl. Plt.—57)

The present invention relates to a new and distinct variety of azalea plant which was originated by us by crossing the azalea variety known as "Julius Roehrs" (unpatented) with the azalea variety known as "Ernest Van Eckhout" (unpatented), the former being the seed parent, and the latter being the pollen parent.

As the result of this breeding, we have produced a new and improved azalea variety which is endowed with the following unique combination of characteristics which are outstanding therein and which distinguish the same from its parents, as well as from all other varieties of which we are aware:

(1) A very heavy texture of the flower petals which appear almost as if waxed;

(2) A slow opening habit of the flowers, with consequent longer than normal flower life; and (3) A distinctive and attractive bright red general color tonality of the flowers corresponding to Cardinal Red in both the bud and open flower stages.

Our new azalea variety cannot be fairly compared with any other variety, since it is superior to all other varieties known to us by reason of its brighter red flower color and the unusually heavy texture and waxy appearance of the flower petals, while taking a week or more for the flowers to open from colorful buds, thereby assuring much longer life in flower shops than most other varieties.

Asexual reproduction of our new variety by cuttings, as performed by us at Whittier, Calif. shows that the foregoing characteristics and distinctions come true to form and are established and transmitted through succeeding propagations.

The accompanying drawings shows a typical specimen plant of our new azalea variety, as well as typical specimens of the flowers and foliage on a somewhat enlarged scale, all as depicted in color as nearly true as it is reasonably possible to make the same in a color illustration of this character.

The following is a detailed description of our new variety, with color terminology in accordance with the Horticultural Colour Chart issued by Wilson Colour Ltd. in collaboration with The Royal Horticultural Society, except where general color terms of ordinary dictionary significance are obvious:

Locality where grown and observed: Whittier, Calif.

Propagation: Holds its distinguishing characteristics through succeeding propagations by cuttings.

*Plant*

Form: Bush; much-branched.

Habit: Vigorous; branching.

Rooting: Good.

Blooming season.: From Christmas through spring season.

Forcing: Good suitability.

Foliage:

*Size.*—From large to medium.

*Quantity.*—Normal.

*Color.*—New foliage: upper side— Scheele's Green, Plate 860, page 175; under side—Scheele's Green, Plate 860/1, page 175. Old foliage: upper side—Spinach Green, Plate 0960, page 187; under side—Spinach Green, Plate 0960/1, page 187.

*Shape.*—Oval.

*Texture.*—Upper side—glossy; smooth. Under side slightly rough.

*Margin.*—Smooth edge.

*Aspect.*—Good.

*Disease resistance.*—Good resistance to ordinary diseases to which azalea plants are normally subject, as determined by comparison with other varieties grown under the same cultural conditions at Whittier, Calif.

*Flowers*

Borne: Two or three to stem.

Quantity of bloom: Free, both outdoors and in greenhouse.

Continuity: One season. Permanence—long lasting; do not shatter.

Petalage:

*Number of petals under normal conditions.*—5 upper petals and 5 lower petals.

*Color.*—Cardinal Red, Plate 822/1, page 168.

*Texture.*—Very heavy; petals appear almost as if waxed.

*Appearance.*—Inside—double hose-in-hose, with tufted center. Outside—rather fuzzy apperance on outside of bud before flower opens.

*Shape.*—Almost round.

*Arrangement.*—Double hose-in-hose, with tufted center.

*Size.*—About 3 inches in diameter.

Bud: Quite wavy at times, resembling a rose bud, before it opens. Color—same as open flower.

*Reproductive organs*

Stamens: Very few seen. Color—red.

Pollen: Sparse. Color—Yellow.

Styles: Very small. Color—red.

Ovaries: Very poorly developed.

We claim:

A new and distinct variety of azalea plant, substantially as herein shown and described, characterized particularly as to novelty by the unique combination of a very heavy texture of the flower petals which appear almost as if waxed, a slow opening habit of the flowers, with consequent longer than normal flower life, and a distinctive and attractive bright red general color tonality of the flowers corresponding to Cardinal Red in both the bud and open flower stages.

No references cited.

ROBERT E. BAGWILL, *Primary Examiner.*